(12) United States Patent
Bachelder et al.

(10) Patent No.: US 6,636,298 B1
(45) Date of Patent: Oct. 21, 2003

(54) METHOD AND APPARATUS FOR FOCUSING AN OPTICAL INSPECTION SYSTEM

(75) Inventors: Ivan Bachelder, Newton, MA (US); Yusuf Akgul, Northboro, MA (US); Prabhav Morje, Natick, MA (US); Juha Koljonen, Needham, MA (US)

(73) Assignee: Cognex Technology and Investment Corporation, Mountain View, CA (US)

( * ) Notice: Subject to any disclaimer, the term of this patent is extended or adjusted under 35 U.S.C. 154(b) by 0 days.

(21) Appl. No.: 10/024,404

(22) Filed: Dec. 18, 2001

(51) Int. Cl.7 .............................................. G01N 21/00
(52) U.S. Cl. ...................................................... 356/73.1
(58) Field of Search ........................ 356/73.1; 382/108, 382/152, 141–150, 173, 180, 254, 260, 276, 307; 250/559.04–559.08; 348/125–134

(56) References Cited

U.S. PATENT DOCUMENTS

| | | |
|---|---|---|
| 5,179,419 A | 1/1993 | Palmquist et al. |
| 5,319,734 A | 6/1994 | Buzzetti |
| 5,535,002 A | 7/1996 | Csipkes et al. |
| 5,543,915 A | 8/1996 | Csipkes et al. |
| 5,596,672 A | 1/1997 | Harman et al. |
| 5,600,439 A | 2/1997 | Csipkes et al. |
| 5,636,020 A | 6/1997 | Csipkes et al. |
| 5,657,131 A | 8/1997 | Csipkes et al. |
| 5,671,049 A | 9/1997 | Csipkes et al. |
| 5,727,327 A | 3/1998 | Wakabayashi et al. |
| 5,729,622 A | 3/1998 | Csipkes et al. |
| 5,729,966 A | 3/1998 | Grulick |
| 5,768,401 A | 6/1998 | Csipkes et al. |
| 5,768,409 A | 6/1998 | Csipkes et al. |
| 5,809,162 A | 9/1998 | Csipkes et al. |
| 5,857,047 A | 1/1999 | Strand et al. |
| 5,857,049 A | 1/1999 | Beranek et al. |
| 5,862,250 A | 1/1999 | Csipkes et al. |
| 5,898,494 A | 4/1999 | Csipkes et al. |
| 5,923,781 A | 7/1999 | Csipkes et al. |
| 5,995,212 A | 11/1999 | Dar et al. |
| 6,069,991 A | 5/2000 | Hibbs-Brenner et al. |
| 6,088,498 A | 7/2000 | Hibbs-Brenner et al. |
| 6,105,396 A | 8/2000 | Glodis et al. |
| 6,183,343 B1 | 2/2001 | Buzzetti |

OTHER PUBLICATIONS

Evan Lubofsky, Machine vision takes guesswork out of fiber–polishing inspection, Laser Focus World, Sep., 2001.

*Primary Examiner*—Tu T. Nguyen
(74) *Attorney, Agent, or Firm*—Arthur J. O'Dea

(57) ABSTRACT

A method is provided for obtaining a focused image of an object in an application of machine vision in an optical inspection system. A coarse focus setting is first obtained by maximizing a coarse feature sharpness measurement performed on an image of the object of inspection. Then, a fine focus setting is obtained by maximizing a fine feature sharpness measurement performed on a portion of an image of the object of inspection. Finally, the fine focused image can be further analyzed, inspected, or otherwise processed.

25 Claims, 6 Drawing Sheets

METHOD AND APPARATUS FOR FOCUSING AN OPTICAL INSPECTION SYSTEM

BACKGROUND OF THE INVENTION

This invention relates to the field of machine vision, and its application in obtaining an optimally focused image of an object under analysis. Specifically, the invention addresses a need for obtaining a properly focused image under high magnification of a portion of a surface. The invention is suitable for the inspection of transparent and/or translucent surfaces, and surfaces that are not coplanar, though, it can be used to inspect the surface of virtually any object.

Inspection operations in an industrial environment are typically performed to characterize manufacturing operations, and to ensure that quality and product specification requirements are met. Many inspection operations can be extremely tedious for human operators performing manual inspection, and the application of machine vision is typically used to improve the consistency and accuracy of an inspection operation, while relieving an inspection operator from performing the task. For example, the application of machine vision-assisted inspection of fiber optic cable assemblies has recently been the subject of much development.

Fiber optic cable assembly operations require the inspection of fiber optic cable end faces to ensure that fiber connections do not degrade optical signal transmission. Scratches, cracks, and debris on critical areas of the interconnection interface may result in defective operation, or result in a degradation of performance. High-magnification inspection of the fiber end face is typically performed during assembly to inspect the condition and cleanliness of the fiber.

Inspection of the end face of a fiber optic cable is inherently difficult because of the properties and characteristics of the fiber. The regions of the fiber end face that require inspection are generally transparent, and exhibit low contrast of features when imaged for machine vision applications. The transparent nature of the fiber optic cable contributes to difficult lighting conditions since illumination intended for inspection of the surface also enters the fiber, and may reflect back into the machine vision system causing image noise. Moreover, images of similar fiber ends typically appear significantly different under identical lighting conditions.

Automation of the inspection of fiber optic cable end faces using machine vision improves inspection efficiency, and to minimizes or avoids the subjectivity of human assessment. Effective implementation of machine vision in an automated inspection process requires a properly focused image of the area under analysis. Manually focused, fiber end face images are subject to human inspection error and result in unrepeatable results. For example, scratches, pits, and other defects appear brighter and/or larger when the image is out of focus, since the features of the potential defect are blurred, which may result in a false rejection of an otherwise acceptable fiber. Therefore, an automated inspection process having an automatic focus mechanism is preferred for uniform, and optimal results.

The prior art suggests the use of an image sharpness measurement to attain an optimal focus setting for an inspection operation of a planar optical fiber end face surface. This has been done by searching through several images at various focus settings and measuring a gradient magnitude of features, such as the fiber boundary and other features, in each image, and calculating a sharpness response. Selecting the focus setting so as to obtain a maximum sharpness response results in an optimal focus setting for the found features. However, the surface of a fiber end face in the current state of the art is not typically planar. Proper focus settings for fiber boundary features will not result in an optimal focus setting for the entire non-planar fiber surface.

Characteristics of a transparent, non-planar surface, such as a non-planar fiber optic end face, present additional challenges to focusing the image for inspection. Defects, such as scratches and contamination, are not visible when the image is out of focus. A narrow depth of field at high magnifications further complicates the inspection process since regions of an image may appear to be properly focused while other portions of the image exhibit improper focus. The sharpness response for fine, non-structural features, is extremely narrow, to the extent that a focus adjustment increment must be extremely small in order to detect a perceptible change in the sharpness response. Such small focus adjustment increments are difficult and often not possible for a human operator to perform in a manner that is consistent, reliable, and not subject to variable human interpretation.

BRIEF SUMMARY OF THE INVENTION

In one general aspect of the present invention, a method is provided for determining an optimal focus setting of an optical imaging system comprising a coarse focus, followed by a fine focus. The coarse focus is attained by providing an image of an object under inspection through a range of possible focus settings, and measuring a sharpness response of the image. The coarse focus setting is determined when the sharpness response is measured to be at a maximum value. The fine focus is attained by starting at the coarse focus setting, and providing an image of the object under inspection through a range of possible fine focus settings, and measuring the fine feature sharpness response. The fine feature sharpness response can be determined from a portion of the image for which the optimal focus setting is desired. The optimal focus setting is determined when the fine feature sharpness response is measured to be at a maximum value.

In accordance with another aspect of the invention, the method for determining an optimal focus setting can be applied to the inspection of a fiber optic end face. The coarse focus setting can be best determined by finding the interface between layers in the fiber, which appear as an annular feature in the image, and measuring an edge characteristic, such as by applying a caliper tool to the feature in the image, to measure sharpness.

A further aspect of the invention measures coarse feature sharpness using sub-pixel boundary gradient magnitude of features associated with overall structure of the object under inspection. Sub-pixel boundary gradient magnitude can be easily determined by running conventional edge detection techniques commonly used in machine vision.

A still further aspect of the invention measures fine feature sharpness by associating a sharpness measurement to the amount of image detail present in the portion of the image for which the optimal focus setting is desired. This can also be determined by transforming the image into frequency space, and measuring the density of high frequency elements through the application of a band pass filter.

A still further aspect of the invention contemplates the use of more than one image of the object at a particular focus setting for the calculation of the sharpness measurement. A sharpness measurement can be determined by comparing the multiple images.

As another aspect of the invention, an apparatus for focusing an optical inspection system comprises a camera, an object of inspection, a focus adjusting mechanism, and a machine vision processor, for carrying out the method of the present invention. The machine vision processor has a coarse feature sharpness measuring capability for measuring coarse feature sharpness of the overall structure of the object of inspection, that cooperates with the focus adjusting mechanism. The machine vision processor has a fine feature sharpness measuring capability for measuring fine feature sharpness of the surface of the object of inspection, also cooperative with the focus adjusting mechanism. The machine vision processor has a signaling capability for indicating maximum values for the coarse feature sharpness measurement and the fine feature sharpness measurement.

Still other advantages of the present invention will become readily apparent to those skilled in the art from the following detailed description. As will be realized, the invention is capable of other and different embodiments, and its several details are capable of modifications in various obvious respects, all without departing from the invention. Accordingly, the drawing and description are to be regarded as illustrative in nature, and not as restrictive.

BRIEF DESCRIPTION OF THE SEVERAL VIEWS OF THE DRAWING

The invention will be more fully understood from the following detailed description, in conjunction with the accompanying figures, wherein:

FIG. 2b is a cross-sectional view of the fiber optic cable represented in FIG. 2a.

DETAILED DESCRIPTION OF THE INVENTION

Figure 1:
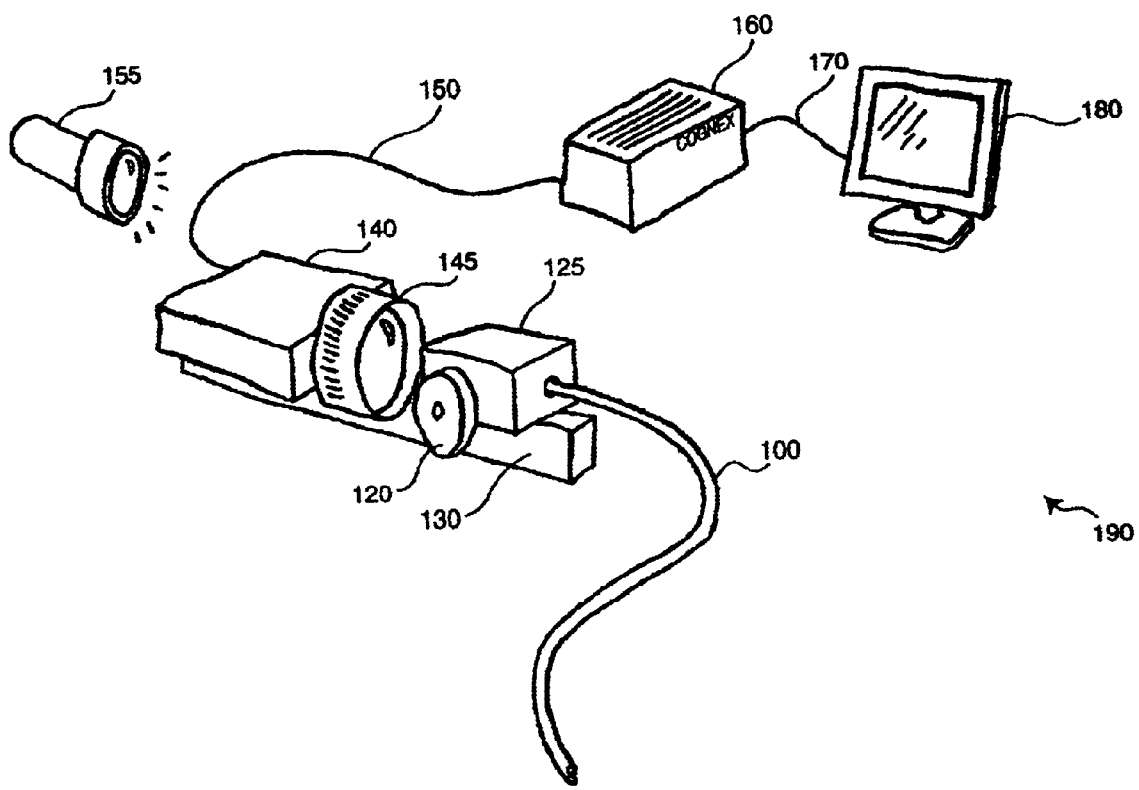
FIG. 1 is a depiction of an apparatus for the inspection of a fiber optic cable end.

FIG. 1 depicts a fiber optic fiber end inspection system 190 used to inspect the end face of a fiber optic cable 100. A camera 140 having a lens 145 is mounted to an inspection frame 130 and directed to an inspection fixture 125. The fiber optic cable 100 end face is presented to the lens 145 by inserting the fiber optic cable 100 end into the inspection fixture 125. A typical fiber optic end inspection system 190 will employ a microscope adapted for inspection of fiber, or fiberscope, to provide significant magnification of the fiber optic cable 100 end as it is presented to the lens 145 of the camera 140. The fiber optic cable 100 end face is illuminated by a light source 155. The inspection fixture 125 has a focus adjustment mechanism 120 that facilitates translation of the inspection fixture 125 relative to the camera 140 and inspection frame 130. Rotation of the focus adjustment mechanism 120 changes the distance between the lens 145 and the inspection fixture 125. One skilled in the art will appreciate that alternate embodiments exist where the camera 140 or lens 145 can be moved relative to the inspection fixture 125 to adjust positioning and/or focus of the inspection system 190.

The camera 140 is coupled to a machine vision processor 160 through an image data transmission cable 150. The machine vision processor 160 acquires an image of a portion of the fiber optic cable 100 end and performs an analysis of the image to perform an inspection. A display 180 is coupled to the machine vision processor 160 through a display cable 170 so that the image, focus parameters, and the result of the inspection can be reported to an operator.

Figure 2A:
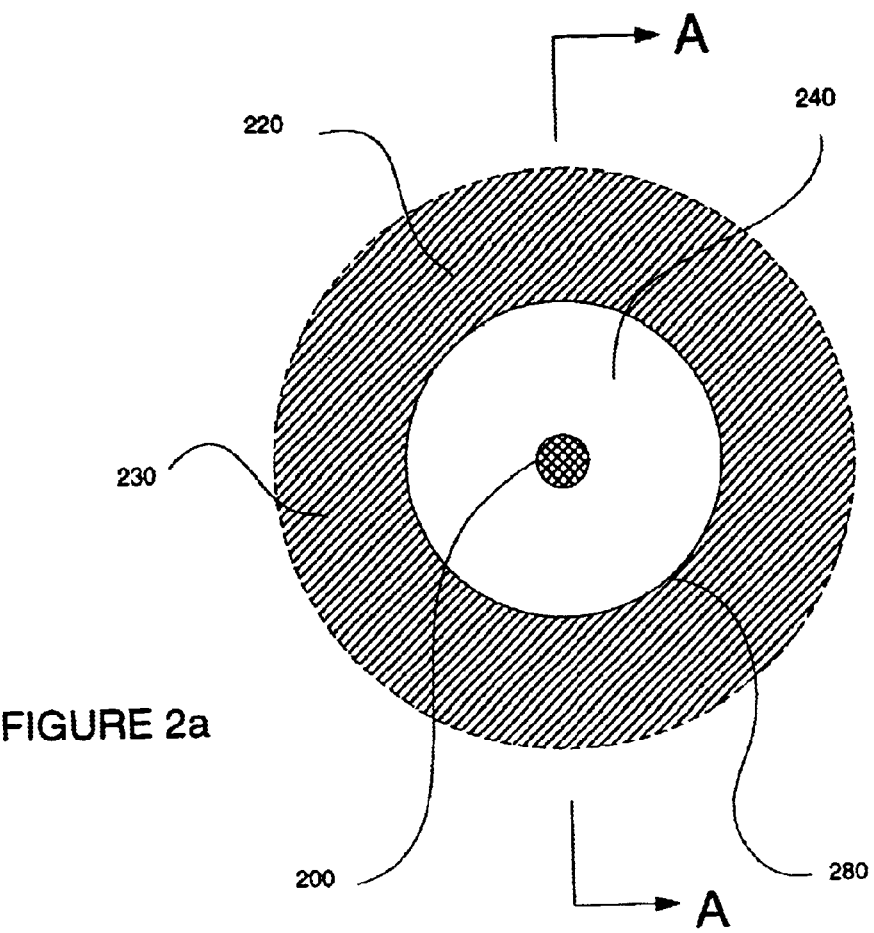
FIG. 2a is a plan view of the end of a fiber optic cable.

The fiber optic cable 100, as viewed by the camera 140 in the fiber end inspection system 190, is depicted in FIG. 2a. The fiber optic cable 100 has a core 200, through which an optical signal is transmitted in operation. The core 200 is surrounded by a cladding 240, and a buffer 220. The optical signal transmitted through the core 200 is propagated by internal refraction as known in the art, as it reflects off the cladding 200 that is positioned around the core 200. The core 200 is made of pure glass drawn out into a fine strand. The cladding 240 is one or more layers of doped glass, which are doped to have a lower index of refraction than the core 200. Thus, the cladding 240, as known in the art, causes the optical signal to be directed back into the core. The buffer 220 surrounds the cladding to isolate and protect the core 200 and cladding 240. Additional shielding and insulation is typically applied for further protection.

Fiber optic cable is classified by transmission type, where transmission types include single-mode or multi-mode, for example, where mode is a term known in the art. Single-mode cable is used to transmit one mode of light, where multi-mode fiber acts to transmit a broader bandwidth of light in the form of a multiplexed optical signal. Typically, the diameter of the core 200 of multi-mode fiber is larger than single mode fiber. Multi-mode fiber core is approximately 62 microns in diameter, while single mode fiber core is approximately 8 microns in diameter, at the current level of technology. Both types of cable have a cladding diameter of typically 125 microns.

Within a fiber optic system, the fiber optic cable 100 is cut and connected or spliced to other fibers, transmitters, and/or receivers, with various connector configurations. After cutting the core 200, the cladding 240, and any surrounding layers present at, or near, the fiber optic end face are polished by processes and techniques known in the art, to form a termination. Typically, the termination is inspected after polishing, or during routine maintenance or cleaning, and after connecting or disconnecting fibers.

Figure 2B:
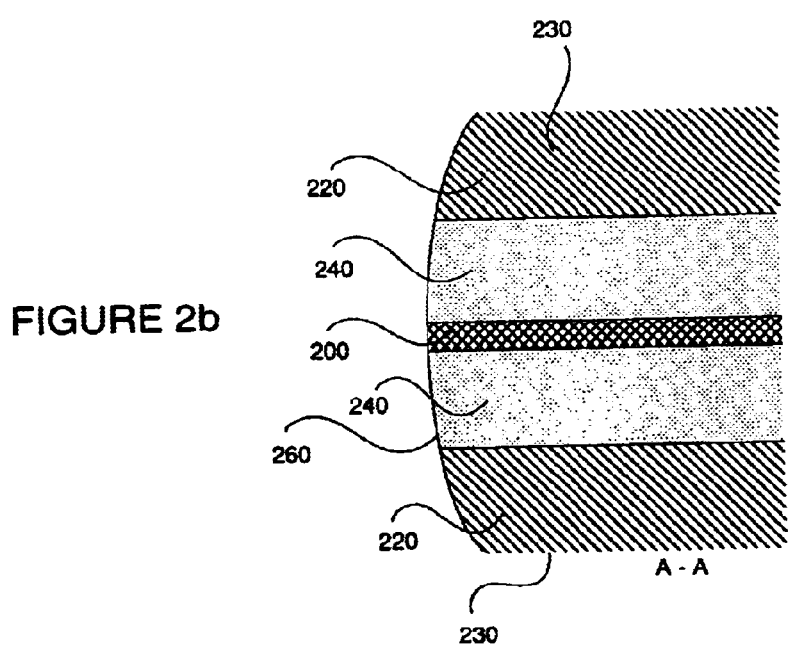

A fiber optic cable 100 termination will typically employ a ferrule 230 for supporting the fiber in place of the buffer 220. An annular interface region 280 forms the interface between the cladding 240 and the buffer 220 or ferrule 230. FIG. 2b depicts a cross-sectional view of the fiber optic cable 100 through section A—A of FIG. 2a. The fiber end surface 260 can be polished, and is typically not flat, having a slight curvature, as shown in FIG. 2b. Various fiber optic cable 100 end configurations exist having similar non-planar end profiles. During an inspection of the fiber end surface 260 at high magnification, the curvature prevents the fiber optic fiber end inspection system from obtaining an image of a portion of the fiber end surface 260 that is completely in-focus.

Figure 3:
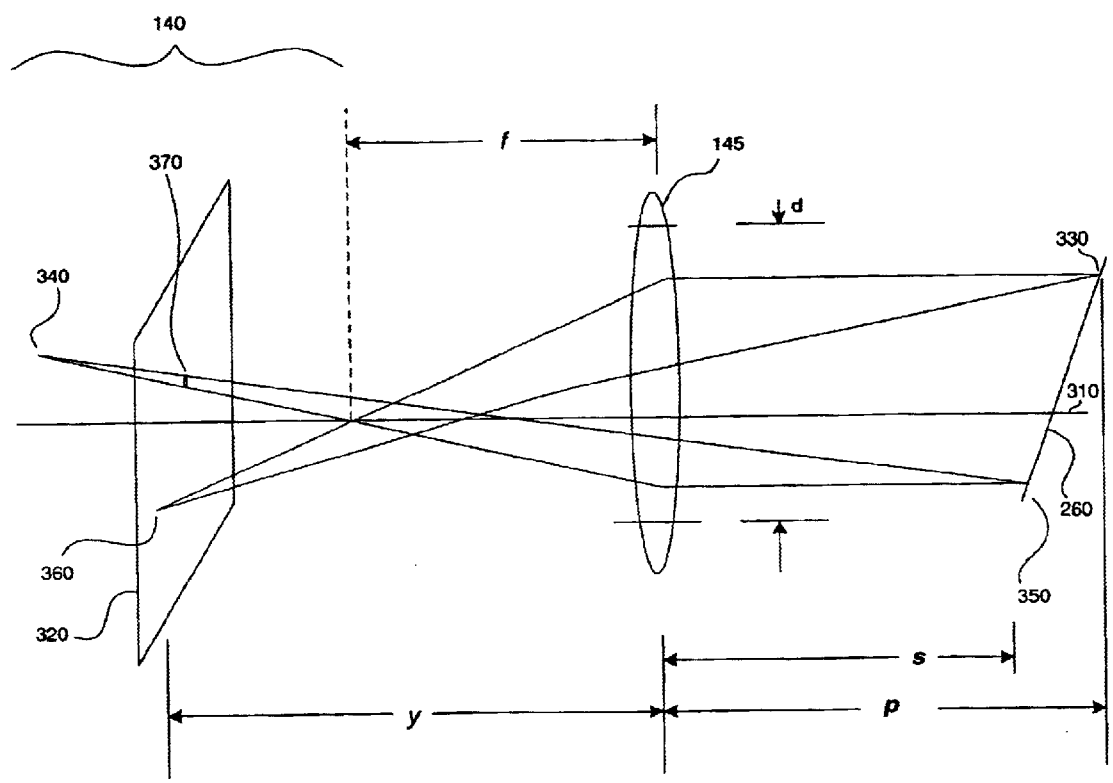
FIG. 3 is a schematic view of a portion of the apparatus of FIG. 1.

Portions of the fiber optic end inspection system 190 are modeled schematically in FIG. 3, and explained fundamentally herein, though it is commonly known in the art that several optical models that can be applied to such an inspection system. The lens 145 having a focal length f projects an image of a portion of the fiber optic end surface 260 on a CCD (Charge Coupled Device) sensor 320 in the camera 140 along an optical axis 310. Alternate embodiments to the CCD sensor can include an array of photosensors, or other sensors known in the art. A sharp image of a portion of the fiber optic end surface 260 can be formed on the CCD sensor 320 according to the thin lens equation where p is the distance from the lens 145 to the fiber optic end surface 260 and v is the distance from the lens 145 to the CCD sensor 320 in the camera 140:

$$(1/p)+(1/v)=(1/f)$$

A sharp image of a portion of the fiber optic end surface 260 represented by reference numeral 330 is formed on the CCD sensor 320 represented by reference numeral 360. If the object is positioned at a distance s for a given focus adjustment v, as represented by reference numeral 350, a circle of confusion 370 forms on the CCD sensor 320, which results in an out-of-focus image. The circle of confusion 370 diameter can be calculated as:

$$C = \left| f * d * \left(\frac{p}{s} - 1\right) * (p - f) \right|$$

where d is the aperture diameter, p is the object distance to the lens for a perfect focus, and s is the distance from the lens to the object to be imaged as represented by reference numeral 350.

An image of a portion of the fiber optic end surface 260 is formed on the CCD sensor 320 by combining the circles of confusion, e.g., reference numeral 370, corresponding to each point on the fiber optic end surface 260, e.g., reference numeral 350. If the image is significantly out of focus $|p-s|\gg 0$, that portion of the image will be affected mostly from the general structure (low frequency structure) in the scene. This general structure contributes to the low frequency structure of the image for all values of s. Small changes in s will not critically affect features corresponding to the general structure of the image. As the image of a portion of the fiber optic end surface 260 nears sharp focus, i.e., $|p-s|\equiv 0$, the image will be affected from the fine structure (high frequency structure) in the scene. Any small change in s will result in a considerable response from the fine structure in the image.

Figure 4:
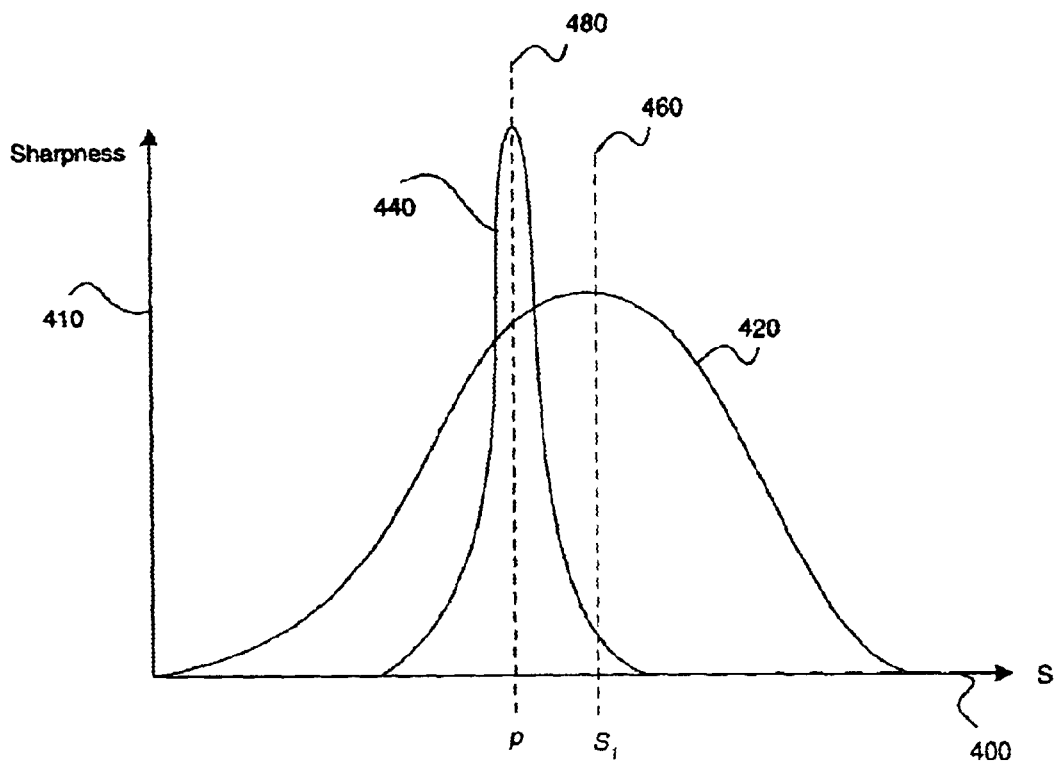
FIG. 4 is a graphical representation of the relationship of the sharpness of features in the image of a non-planar surface to a focus position.

FIG. 4 graphically depicts the relationship of a sharpness response of an image as a function of the position s of the fiber optic end surface 260 relative to the lens 145 of the camera 140. A coarse feature sharpness response 420 associated with the low frequency structure has a maximum coarse feature sharpness 460 at focus position $s_1$. A fine feature sharpness response 440 associated with the high frequency structure has a maximum fine feature sharpness 480 at the optimal focus position p. The coarse feature sharpness response 420 is more broad and flat than the fine feature sharpness response 440. A typical fiber optic end surface 260 displays such a bi-modal sharpness response, where the fine feature sharpness response 440 is monotonically increasing or decreasing at $s_1$, and the fine feature sharpness response 440 does not have any local extrema between the maximum coarse feature sharpness 460 at $s_1$ and p. The maximum coarse feature sharpness 460 can be difficult to accurately determine due to noise in the image.

Figure 5:
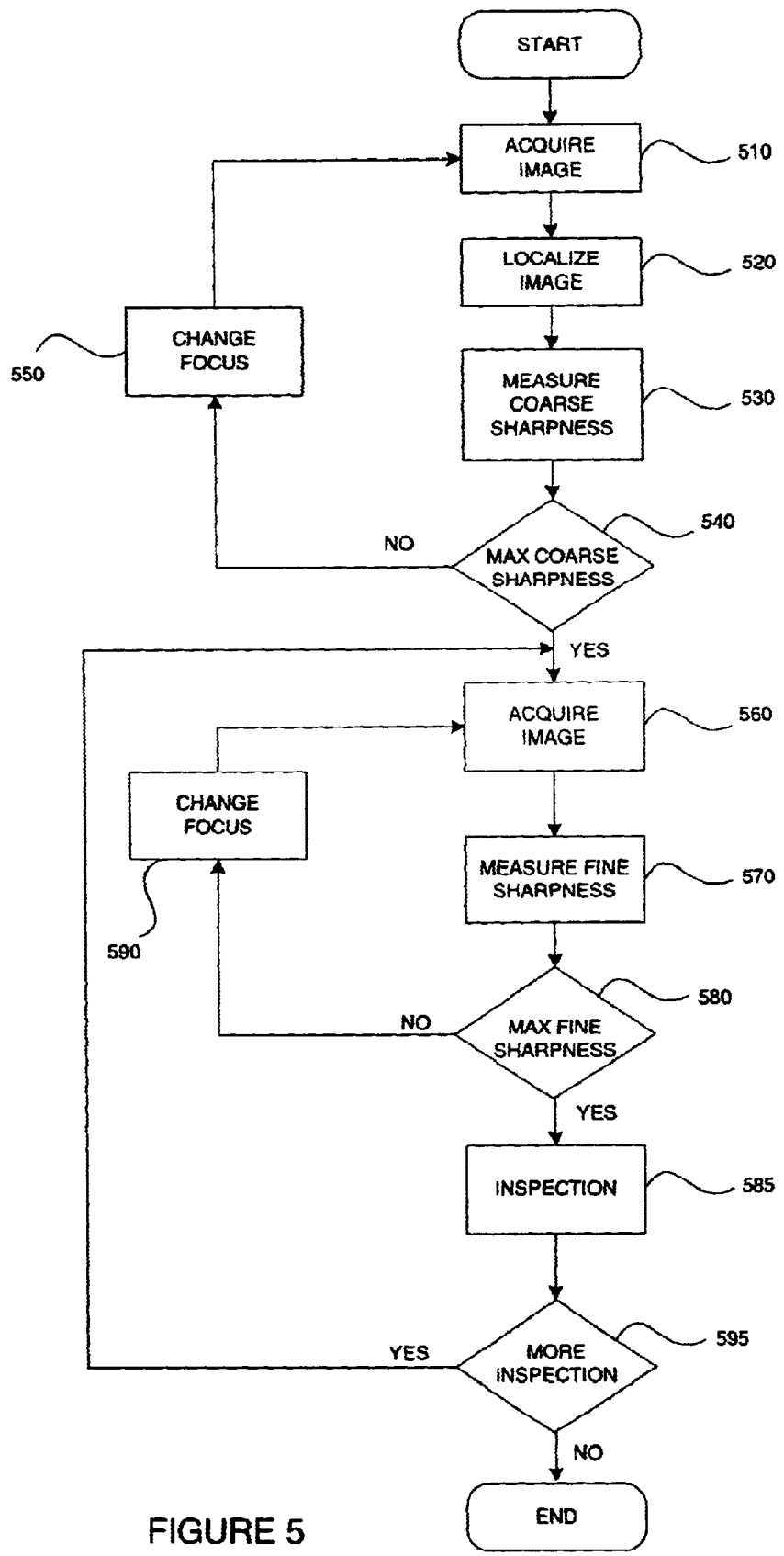
FIG. 5 is a flowchart of the method of the present invention.

FIG. 5 describes the method of the present invention in its preferred embodiment. The fiber optic inspection system 190 is configured to present the fiber optic cable 100 to the camera 140. The steps of the method described in FIG. 5 are performed over a range of possible focus settings of various distances from the fiber optic cable 100 to the lens 145 of the camera 140. The machine vision processor 160 acquires an image of a portion of the fiber optic end surface 260, according to step 510.

Step 520 localizes the image to include only the region containing structure elements of the fiber optic cable 100 in the image of a portion of the fiber optic end surface 260. In the preferred embodiment, the annular interface 280 between the cladding 240 and the ferrule 230 is the most consistent and reliable feature to locate for a coarse focus adjustment. This feature 280 can be interpreted as a circular pattern to which standard machine vision search tools can be applied using a number of alternative techniques. For example, normalized correlation search, including one that uses templates at a variety of rotations and scales, may be used. Alternatively, a geometric feature-matching search tool capable of aligning several degrees of freedom, such as translation, rotation, and scale, may be used. A further possibility for the localization step 520 is to employ the Generalized Hough Transform, including extensions of which that are scale-invariant and orientation-invariant, as is known in the art. The use of any alignment technique is within the scope of the present invention. In a preferred embodiment, a geometric feature-matching tool, such as PatMax® from Cognex Corporation, can be trained on a circular model of the interface between the cladding 240 and the ferrule 230 to find an annular interface region 280.

Step 530 measures a coarse feature sharpness of the localized image of step 520. The coarse feature sharpness can be represented as the diameter of the circle of confusion 370 in the image of the structure of the fiber optic end surface 260. In the preferred embodiment, an assessment of the edge features of the found annular interface region 280 can be made to represent a sharpness measurement.

The caliper tool from Cognex Corporation can be applied to the found annular interface region 280 to provide a numerical assessment of the sharpness of the edge features of the found annular interface region 280. In the preferred embodiment, approximately one hundred caliper tools are placed at evenly spaced intervals over the circumference of the annular interface region 280. Each tool scores the contrast of the transition from the cladding 240 to the ferrule 230. A higher score is expected in the assessment of a clearly defined, sharply focused transition.

A maximum average caliper score measurement indicates a maximum sharpness measurement, since the diameter of the circle of confusion 370 of the edge features of the interface between the cladding 240 and the ferrule 230 in the image of step 520, approaches zero.

Alternatively, the coarse feature sharpness measurement can be determined using standard edge detection techniques. The acquire image of step 510 preferably includes filtering or smoothing to remove fine structure of the acquired image. A mask must be generated to remove features not associated with the annular interface region 280 to be found in the localization step 520. Edge detection then can be applied to the filtered and masked image to return edgelets and their magnitudes. A coarse feature sharpness measurement can be represented by the summation of the magnitudes. As the structure features are brought into focus, the contrast of the edges in the image will increase. A maximum contrast of the structure features can be associated with a sharpness measurement, indicating an optimal coarse focus.

Step 540 compares the coarse feature sharpness measurements of step 530 with the coarse feature sharpness measurements made at other focus settings. When sharpness measurements are absolute, images must be acquired at more than one respective focus setting for a maximum sharpness value to be determined. If sharpness measurements are relative, only one image at a single focus setting is necessary for comparison. Step 540 initiates a loop that repeats steps 510, 520, and 530 for the range of possible focus settings, while retaining the value of the maximum sharpness measurement. Step 550 changes the focus setting in the range of possible focus settings in the loop to determine the maximum coarse feature sharpness measurement. The loop terminates when a maximum sharpness measurement has been identified, and step 560 is performed with the fiber optic inspection system 190 set to the focus setting having the maximum coarse feature sharpness measurement of step 530.

Focus adjustment step 550 can be performed several ways. The most basic method is the most exhaustive; sharpness scores can be stored for images acquired at a complete range of focus settings with a reference to the focus setting. Comparison of the sharpness measurements of step 530 can be performed on the stored values, and the focus setting that produces the maximum sharpness score is selected for further processing.

A more sophisticated and efficient method is commonly known as hill-climbing, or gradient descent. The sharpness measurements of step 530 are performed on two images of different focus settings. A comparison of the two sharpness measurements (a form of relative sharpness measurement) can be performed to determine the direction for the focus adjustment to expect an increased sharpness measurement. Optionally, a measure of the magnitude of difference between the sharpness measurements can be used to determine the extent of focus adjustment; i.e., the focus adjustment step can be proportional to the difference between the sharpness measurements. This process continues until the maximum sharpness is determined at step 540.

A third method of adjusting the focus setting of step 550 is a bisection method. The pass through the loop of steps 510, 520, 530, and 540 is performed at a first extreme end of the focus range. The second pass through the loop of steps 510, 520, 530, and 540 is performed at the opposite extreme end of the focus range. The third pass is performed at an approximate midpoint. Subsequent passes through the loop are performed at a focus setting that is the approximate midpoint between the focus settings returning two highest sharpness scores of the images from the three preceding focus settings.

The system 190 is set to the focus setting returning the maximum coarse feature sharpness score from step 540, so that the method of FIG. 5 can proceed to step 560, where the machine vision processor 160 acquires a second image of a portion of the fiber optic end surface 260. The image acquired at step 560 for further processing can be limited to the region or zone in the fiber end surface 260 to which inspection is sought. It is optional that a localization step be performed after image acquisition at step 560, since the focus adjustment is so minimal, that the features associated with the object structure will not move.

Conventional machine vision techniques may be employed for inspection of specified regions of the image. User input can provide inspection criteria for specific regions of the fiber optic end surface 260, relative to a reference position, such as the core 200 or annular interface region 280. A pose of the fiber optic end surface 260 can be provided from the localization step 520 in the method. Often, the most critical area for inspection of surface scratches and cracks is the core 200. Accordingly, a pose of the core 200 in the image can be provided for the application of conventional machine vision processing in inspection. Since the fiber optic end surface 260 is typically non-planar, and the high magnification of the image results in a narrow depth of field in the image, only a portion of the surface can be optimally focused. Subsequent steps are therefore presumed to apply to the region or zone in the fiber end surface 260, to determine an optimal focus for that region or zone.

A fine feature sharpness measurement is then taken from the image according to step 570. A measurement of fine feature sharpness can be based on the amount of image detail in the region or zone in the image of step 560. The amount of image detail is directly proportional to the number of edgelets detected by a machine vision edge detection algorithm.

Alternatively, the fine feature sharpness measurement can be attributed to the amount of information in the region or zone in the image of step 560. A measured entropy calculation can be performed on the image of step 560 to provide a score or fine feature sharpness measurement. A mask is generated to expose only the region of interest. The image entropy score for an image having pixel coordinates i, j can by calculated by:

$$-\sum_i \sum_j P(i, j) \log(P(i, j))$$

where P is the probability that a given greylevel or intensity exists for the pixels in the image. An image having little detail, i.e., few fine features, with a narrow distribution of greylevels, such as a blurry, out-of-focus image, will return a low entropy score. An image that is optimally focused, will return a relative higher entropy score, since fine featured detail in the image has a broad distribution of pixel intensity greylevel values.

Fine feature sharpness can also be measured by transforming the image of step 560 into frequency space, using techniques known in the art (such as FFT (Fast Fourier Transform), and measuring the density of high frequency components of the power spectrum image. Each point in the image of step 560 can be represented by a sum of spatial frequencies. Low frequency components describe general structure of the image, while high frequency components are associated with sharp edges of features and the fine detail in the image. An out-of-focus image will display blurred edges, and will therefore exhibit a low density of high-frequency components in the power spectrum of the image. As the image is brought into focus, and edges become more clearly distinct, high frequency components will emerge in frequency space. An image that is brought into perfect focus will exhibit a maximum density of high frequency components in a frequency space representation of the image.

The fine feature sharpness measurement of step 570 can be represented by a numerical calculation or score of the pose, region, or zone of the image. This calculation, or score, can be associated to the focus setting of the image acquired at step 560, and is compared to the other calculations, or scores, measured for images acquired at step 560 for other focus settings at step 580.

A maximum fine feature sharpness measurement indicates that an optimum focus setting has been attained. Step 580 initiates a loop of acquiring an image at step 560, and measuring the fine feature sharpness of 570, within a possible range of focus settings. The focus setting is changed at step 590 if a maximum value has not been identified, in a manner similar to the methods discussed for the coarse focus adjustment step 550. It should be noted that the focus adjustment performed at step 590 must be in extremely fine increments, as the fine feature sharpness response 440 can only be detected in a small range of focus settings from the maximum coarse feature sharpness 460 at $s_1$ in FIG. 4.

Inspection of the focused region, or other operation, analysis, or processing, may be performed as indicated at step 585. Alternatively, the images can be stored electronically in memory for later analysis. Further inspection or processing may be performed on other regions of the fiber optic end surface 260 without repeating the entire method described in FIG. 5. As indicated in decision step 595, a new image may be acquired at step 560 with a new pose, region or zone of the fiber optic end surface 260. The inspection method on distinct regions of the fiber end surface 260 can be better understood in conjunction with a description of FIGS. 6 and 7.

Figure 6:
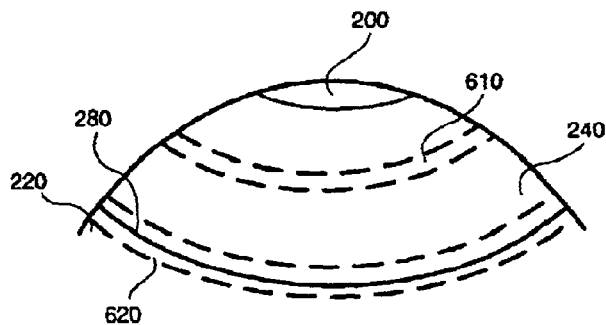
FIG. 6 is an orthogonal view of the end of a fiber optic cable.

FIG. 6 depicts an orthogonal view of the end of a fiber optic cable 100 showing the non-planar surface. The core 200 in the center of the fiber is surrounded by the cladding 240. A ferrule 220 supports the cladding in a typical termination that can be inspected in the inspection system 190. The annular interface region 280 can be used to determine the maximum coarse feature sharpness 460 in the coarse feature sharpness response 420, as described in steps 510, 520, 530, 540, and 550 of FIG. 5. A first region of inspection 610 can be an annular region in the fiber end surface 260 in the cladding 240.

Figure 7:
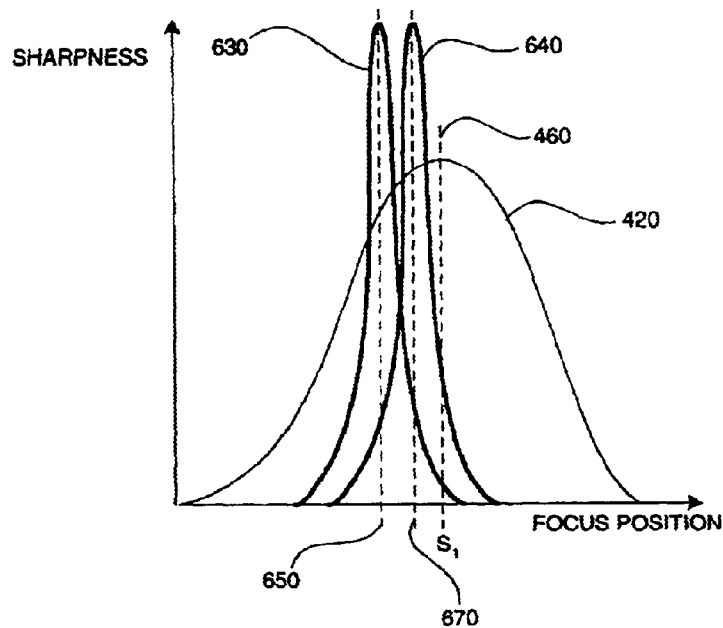
FIG. 7 is a graphical representation of the relationship of the sharpness of features in two regions in the image of a non-planar surface to a focus position.

FIG. 7 is a graphical depiction of the sharpness response of several regions in a non-planar surface over a range of focus positions. A coarse feature sharpness response 420 associated with the low frequency structure has a maximum coarse feature sharpness 460 at focus position $s_1$. The fine feature sharpness response for the first region of inspection 610 can be depicted as a first fine feature sharpness response 640, with a maximum fine feature sharpness at a focus position indicated by numeral 670. The size of the first region of inspection may be limited by the depth of field as a result of the magnification of the inspection system 190. As the focus position decreases, the core region 200, closest to the camera 140, returns a peak in a second fine feature sharpness response 630, with a maximum sharpness at focus position indicated by numeral 650.

The maximum sharpness for the first region of inspection 610 is determined at step 580. The inspection step of 585 is then performed on the first region of inspection 610, since that region is optimally focused. The core 200 is then selected at step 595, and the loop of steps 560, 570, 580, and 590 followed until the core 200 region returns a maximum fine feature sharpness score at step 580. At that point, the core 200 region can be inspected at step 585. It is possible that a fine feature sharpness peak is not detected, if there are no features in the image, indicating that the region of inspection is defect-free.

In the inspection of a fiber optic end surface 160, different defects may be visible or more distinct in the image at different focus positions. For example, to inspect scratches having a certain depth into the fiber optic end surface 160, a focus adjustment can be made for a region, in order to inspect slightly below the surface. While the surface features may lose sharpness, the sharpness response of any scratches in the region of inspection can be expected to increase. For a given region or zone, the surface features can be brought into focus in the first pass prior to decision step 595, and then adjusted to below the surface in subsequent iterations after decision step 595.

An alternate embodiment to which the present invention can be applied is the inspection of optical lenses. Like fiber end faces, optical lenses are not flat and are even more translucent than fiber end faces (to the point of being perfectly transparent under most lighting conditions). Furthermore, it is desirable to detect and precisely measure the lens for defects such as scratches, cracks, chips, and debris, which requires maximally focused images of the defects. In the embodiment directed to lens inspection, a coarse feature sharpness for a lens object can be determined by first aligning a shape modeling the outer boundary of the lens (typically a circle) with the image of the lens obtained at a focus setting at which the lens is visible but not necessarily in focus. For example, one can train a rotation invariant and scale invariant search model for the shape and use the trained model to perform alignment, as can be done with the PatMax tool available from Cognex Corporation or the Hexsight tool available from Adept. A coarse feature sharpness for the lens can then be measured using a method similar to one described for the fiber end application. For example, one can apply a set of caliper tools (e.g. the Caliper Tool available from Cognex Corporation) along the boundary of the aligned shape in the image of the lens, and use the average contrast score of the caliper edge results as the coarse feature sharpness score. A search can then be applied in order to maximize the coarse feature sharpness, with an optional re-alignment step performed before each coarse feature sharpness measurement as needed. The search might, for example, employ a gradient descent technique, as described for the fiber end inspection embodiment and as known in the art. Following the maximization of the coarse feature sharpness score, the fine feature sharpness within a region of the lens can be measured using one of the methods described for the fiber end inspection embodiment, such as the one involving measuring the density of high frequency components in an image transformed into frequency space, or the power spectrum, within a region.

As with fiber end inspection, the non-planar structure of the optical lens may necessitate determining the optimal fine focus position for more than one region of the lens. Due to the transparent nature of the lens, however, there may even be several defects (e.g. cracks) visible at several different focal planes within the glass for a single region. It may therefore be necessary to compute several fine feature sharpness settings within each region, each corresponding to a different focal plane containing defects, so that all defects can be accurately measured. This multi-peak measurement requires a fine focus search strategy other than a simple gradient descent algorithm. For example, it may require a fine feature sharpness peak search that measures the fine feature sharpness for uniformly sampled positions within some range of the optimal coarse feature sharpness peak focus position in order to detect potential fine focus peaks, followed by a separate gradient descent search for each detected peak, each starting with the sampled focus position at which the fine feature sharpness peak was detected. Note that the initial detection of the fine focus peaks is simply a matter of recording those sampled focus positions that yield a fine focus score that is above some minimum fine feature sharpness threshold and is larger than the scores for its neighboring sampled focus positions.

Further still, another embodiment of the invention is an automatic visual inspection of LCD (liquid crystal display) data matrices, which tend to be flat but are somewhat translucent. Reliable LCD data matrix inspection, the purpose of which is to detect scratches and other defects, requires an optimally focused image. Each LCD data matrix is contained in a frame, which provides a structure with respect to which an alignment can be performed in the coarse focus step. An alignment tool for this structure can be trained, for example, by supplying an example image of the display frame (optionally, with a mask image that omits other extraneous features in the image) to a rotation invariant and scale invariant alignment tool, such as PatMax or Hexsight, which can then be employed to align the frame, as commonly known in the art. The coarse feature sharpness score for each focus position can be similarly computed by applying a set of calipers tools along the boundary of the frame, if the dimensions of the frame are known, or by examining the contrast of edges detected within the vicinity of the frame, as described in the fiber end inspection application embodiment. Again, the search for the optimal coarse feature sharpness focus position can be performed in any of the ways previously described, as can the computation of fine feature sharpness and the search for a fine feature sharpness peak within the frame. In this case, it is probably sufficient to optimize the focus position in order to maximize the fine feature sharpness score for only a single region that includes the entire areas within the aligned frame, since an LCD data matrix is typically fairly flat.

Figure 8:
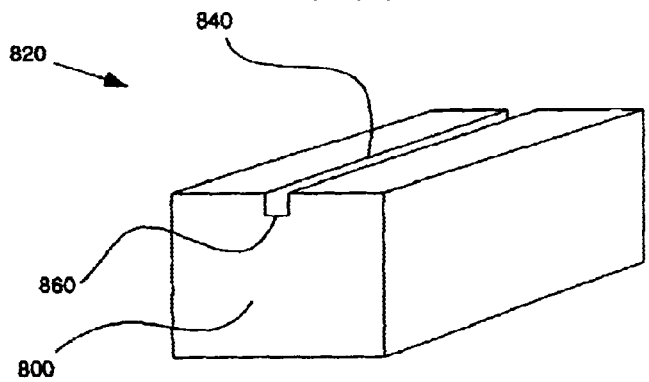
FIG. 8 is an isometric view of a laser diode in an exemplary embodiment of the invention.

In yet another embodiment of the invention, inspection of rectangular laser diodes can be performed, as shown in FIG. 8. Typically, an inspection may be performed to identify defects such as cracks, scratches, debris, and ridges, often called "shingling," caused by non-uniform cutting during the dicing process (wherein the diodes are physically cut from one another from a single wafer). This inspection is especially important in a small region of the laser diode end face 800 from which the end of the wave-guide 840, a trough running along the top side of the laser diode 820, emits precision laser light used to transmit large amounts of data. Again, such inspection requires an optimally focused image. Since the shape of the laser diode is known (i.e. the length, width, and height of the device), a rectangular model of the end face of the diode can be used to train a rotation-scale invariant search tool, such as PatMax or Hexsight, which can then be used to align the model with the image of the laser diode end face 800. Again, any of the techniques described previously can be used for the computation of coarse feature sharpness along the rectangular boundary, the search over focus position for a maximum coarse feature sharpness, the computation of fine feature sharpness within the rectangular boundary, and the search over focus position for the maximum fine feature sharpness. In this embodiment, the fine focus region need only be limited to one region consisting of the rectangular diode end face 800, since it will be nominally flat and opaque, or even some small area around the end of the wave-guide where defects will cause serious problems.

Another embodiment for measuring the attributes of the fine feature sharpness response for a region is to use a standard auto-focus system that employs phase differencing, as employed by many commercially available cameras, and as known by those skilled in the art. An example of one type of phase detection, or phase differencing, is an autofocusing technique implemented in many photographic cameras, such as the one described in U.S. Pat. No. 4,373,791. The technique is based on separating the light rays coming from the objects after they passed through the camera lenses into more than one part, so that they form more than one image. The light ray separation, which can be done by separator lenses or by special photo sensor arrays and CDD's, is performed in such a way that the light rays coming from opposite edges of the camera lens are directed to different images planes or CCD sensors. The image sharpness can be calculated by comparing these images: if the two images are exactly the same, then the focus position is found. As applied to the present invention, the sharpness measurement can be represented as the inverse of the difference between the two images. Additionally the comparison of these images for phase difference of the dominant image structure will indicate if the desired focus plane is in front or behind the current position.

The present invention can employ the phase detection technique as a sharpness measurement, and as a method to determine the focus plane position direction. Special hardware may be necessary in the imaging setup so that light ray separation and the formation of the more than one difference image is possible. The images obtained by the light ray separation are used to determine the how close the focus plane is to the current focus position, which can be considered as a coarse feature sharpness score depending on where the CCD elements of the difference images are placed. Note that, it may not be feasible to use these difference images for an alignment or an inspection process because they can be one-dimensional images or incomplete images. Therefore, after the final focus position is found, or if a full image is necessary for alignment purposes, a separate image on the main CCD is formed independent of the difference CCD's or images.

Generally, the invention can be applied to obtain in-focus images of any relatively flat region of any structure for which an alignment model can be created, and for which coarse feature and fine feature sharpness metrics can be computed. The coarse focus score will be determined by examining the contrast of edges at the high contrast boundaries of the aligned object (though not necessarily the outer boundary), and the fine focus score will be determined by examining the power spectrum or edge contrast within a particular region of the object.

Note that coarse or fine feature sharpness responses might include either absolute or relative measurements of the response without departing from the scope of this invention. For example, one could measure the difference between the sharpness response for a focus position and the sharpness responses of the neighboring focus positions. Even more simply, one could measure whether the sharpness response for a given focus position is higher or lower than the neighboring focus positions. Whether absolute or relative measurements are made, the purpose of the measurements is to determine the focus position at which the sharpness response is maximum, which at minimum requires the direction in which to move the focus position such that the sharpness response becomes larger. Note also that the computation of the maximum coarse feature or fine feature sharpness response is not necessary in order to determine the point at which the response is maximized.

While the invention has been described with reference to the certain illustrated embodiments, the words which have been used herein are words of description, rather than words of limitation. Changes may be made, within the purview of the appended claims, without departing from the scope and sprit of the invention in its aspects. Although the invention has been described herein with reference to particular structures, acts, and materials, the invention is not to be limited to the particulars disclosed, but rather extends to all equivalent structures, acts, and materials, such as are within the scope of the appended claims.

We claim:

1. A method for determining an optimal focus setting of an optical imaging system, the method comprising:
   in a range of coarse focus settings;
      providing a first image of an object at a coarse focus setting;
      measuring a coarse feature sharpness response of the first image;
   setting a coarse focus to provide a maximum coarse feature sharpness response of the first image;
   in a range of fine focus settings from the coarse focus;
      providing a second image of the object at a fine focus setting, the second image having a fine focus area;
      measuring the fine feature sharpness response of the fine focus area; and
   setting the optimal focus to provide a maximum fine feature sharpness response.

2. The method of claim 1 wherein the object is a fiber optic cable end face.

3. The method of claim 2 wherein the step of measuring a coarse feature sharpness further comprises:
   finding an annular interface feature in the first image;
   measuring at least one edge characteristic of the annular interface feature to provide a coarse feature sharpness response.

4. The method of claim 1 wherein the object has a structure feature, and the step of measuring a coarse feature sharpness further comprises finding the structure feature in the first image, detecting at least one sub-pixel boundary gradients, and measuring the at least one sub-pixel boundary gradient magnitude to provide a coarse feature sharpness measurement.

5. The method of claim 1 wherein the step of measuring the fine feature sharpness response of the fine focus area further comprises measuring an image detail of the fine focus area.

6. The method of claim 1 wherein the step of measuring the fine feature sharpness response of the fine focus area further comprises:
   transforming the second image to a frequency space representation of the second image; and
   measuring the density of high frequency elements in the frequency space representation of the second image to provide a fine feature sharpness response.

7. An apparatus for focusing an optical inspection system, the apparatus comprising:
   an object having a structure and a surface;
   a camera for acquiring an image of the object;
   focusing means for adjusting a focal distance between the camera and the object;
   machine vision processor coupled to the camera, comprising;
      a) coarse feature sharpness measuring means, in cooperation with the focusing means, adapted to measure a coarse feature sharpness of at least a portion of the structure in the image; and
      b) fine feature sharpness measuring means, in cooperation with the focusing means and the coarse feature sharpness measuring means, adapted to measure a fine feature sharpness of at least a portion of the surface in the image.

8. The apparatus of claim 7 wherein the object is a fiber optic cable end face.

9. The apparatus of claim 7 wherein the machine vision processor further comprises:
   c) signaling means for indicating a maximum value of the coarse feature sharpness measuring means and the fine feature sharpness measuring means.

10. A method for determining an optimal focus setting of an optical imaging system, the method comprising:
    in a range of coarse focus settings;
       providing at least one first image of an object at a coarse focus setting;
       measuring a coarse feature sharpness response of the at least one first image;
    setting a coarse focus to provide a maximum coarse feature sharpness response of the at least one first image;
    in a range of fine focus settings from the coarse focus;
       providing at least one second image of the object at a fine focus setting, the at least one second image having a fine focus area;
       measuring the fine feature sharpness response of the fine focus area; and
    setting the optimal focus to provide a maximum fine feature sharpness response.

11. The method of claim 10 wherein the object is a fiber optic cable end face.

12. The method of claim 11 wherein the step of measuring a coarse feature sharpness further comprises:
    providing an alignment image of the object from the at least one first image;
    finding an annular interface feature in the alignment image;
    measuring at least one edge characteristic of the annular interface feature to provide a coarse feature sharpness response.

13. The method of claim 10 wherein the object has a structure feature, and the step of measuring a coarse feature sharpness further comprises finding the structure feature in the first image, detecting at least one sub-pixel boundary gradients, and measuring the at least one sub-pixel boundary gradient magnitude to provide a coarse feature sharpness measurement.

14. The method of claim 10 wherein the step of measuring the fine feature sharpness response of the fine focus area further comprises measuring an image detail of the fine focus area.

15. The method of claim 10 wherein the step of measuring the fine feature sharpness response of the fine focus area further comprises:
    transforming the second image to a frequency space representation of the second image; and
    measuring the density of high frequency elements in the frequency space representation of the second image to provide a fine feature sharpness response.

16. A method for obtaining an optimally focused image of the surface of an object, the method comprising:
    acquiring an image of the surface of the object;
    localizing a coarse feature of the surface of the object;
    performing a coarse feature sharpness measurement on the coarse feature;
    using the coarse feature sharpness measurement, determining a maximum coarse feature sharpness measurement;
    using the maximum coarse feature sharpness measurement, acquiring an image of a region of the surface of the object;

performing a fine feature sharpness measurement within the region;

using the fine feature sharpness measurement, determining a maximum fine feature sharpness measurement; and using the maximum fine feature sharpness measurement to determine an optimal focus setting for obtaining an optimally focused image of the surface of the object.

17. The method of claim 16, wherein a maximum fine feature sharpness measurement is determined for each of a plurality of regions of the surface of the object, each such maximum fine feature sharpness measurement being based on a common coarse feature sharpness measurement.

18. The method of claim 16, wherein a maximum fine feature sharpness measurement is determined for each of a plurality of depths for the region of the surface of the object, wherein the object is translucent.

19. The method of claim 16, wherein a maximum fine feature sharpness measurement is determined for each of a plurality of depths for the region of the surface of the object, wherein the object is transparent.

20. The method of claim 16, wherein acquiring the image of the surface of the object includes:

band pass spatial filtering.

21. The method of claim 16, wherein acquiring the image of the surface of the object includes masking.

22. The method of claim 16, wherein the object is an optical fiber end face.

23. The method of claim 22, wherein the coarse feature is an annular interface between two regions of the optical fiber end face.

24. The method of claim 16, wherein performing a coarse feature sharpness measurement on the coarse feature includes detecting and measuring at least one boundary gradient magnitude.

25. The method of claim 16, wherein performing a fine feature sharpness measurement within the region includes:

transforming the region so as to provide a plurality of spatial frequencies of the region;

measuring a density of high spatial frequencies; and using the density of high spatial frequencies so as to provide a fine feature sharpness measurement.

* * * * *